United States Patent
Adler

Patent Number: 6,144,029
Date of Patent: Nov. 7, 2000

[54] METHOD FOR TRACE DETECTION BY SOLVENT-ASSISTED INTRODUCTION OF SUBSTANCES INTO AN ION MOBILITY SPECTROMETER

[75] Inventor: Joachim Adler, Badrina, Germany

[73] Assignee: Bruker-Saxonia Analytik GmbH, Leipzig, Germany

[21] Appl. No.: 09/248,785

[22] Filed: Feb. 12, 1999

[30] Foreign Application Priority Data

Dec. 2, 1998 [DE] Germany ............ 198 05 569

[51] Int. Cl.[7] ........... H01J 49/04
[52] U.S. Cl. ........... 250/288; 250/286; 250/287
[58] Field of Search ........... 250/288, 286, 250/287

[56] References Cited

U.S. PATENT DOCUMENTS

| | | |
|---|---|---|
| 3,970,428 | 7/1976 | Barringer . |
| 4,192,176 | 3/1980 | Barringer . |
| 4,220,414 | 9/1980 | Barringer . |
| 5,083,019 | 1/1992 | Spangler . |
| 5,405,781 | 4/1995 | Davies et al. . |
| 5,425,263 | 6/1995 | Davies et al. . |
| 5,476,794 | 12/1995 | O'Brien et al. . |
| 5,552,600 | 9/1996 | Davies et al. . |
| 5,742,050 | 4/1998 | Amirav et al. ............ 250/288 |

FOREIGN PATENT DOCUMENTS

| | | |
|---|---|---|
| 0 458 622 | 11/1991 | European Pat. Off. . |
| WO 91/02961 | 3/1991 | WIPO . |
| WO 93/06476 | 4/1993 | WIPO . |
| WO 96/37773 | 11/1996 | WIPO . |
| WO 97/38294 | 10/1997 | WIPO . |

*Primary Examiner*—Kiet T. Nguyen

[57] ABSTRACT

The invention relates to a method and an ion mobility spectrometer (IMS) for the detection of contaminations by explosives, drugs, wood preservatives or the like. The substance traces collected on a carrier material, e.g. cellulose, are dissolved in a solvent for detection using an IMS and are vaporized together with this solvent from a sample dispenser in the reaction compartment of the IMS. In this way, the sample dispenser can be operated at a considerably lower temperature.

21 Claims, 4 Drawing Sheets

METHOD FOR TRACE DETECTION BY SOLVENT-ASSISTED INTRODUCTION OF SUBSTANCES INTO AN ION MOBILITY SPECTROMETER

FIELD OF INVENTION

Field of invention is a method for detection of dangerous constituents, particularly of drugs or explosives, in semivolatile substance traces, by means of ion mobility spectrometry using an ion mobility spectrometer (IMS), whereby the substance traces are applied to a carrier material, the carrier material is introduced into a sample dispenser and brought there to a high temperature, whereby the constituents are released from the carrier material and transported by a gas stream into the ion source of the IMS, where molecules from the constituents are ionized by proton or charge transfer and, after passing through a drift chamber in the IMS, are detected and identified.

The invention also includes an IMS to perform the method.

PRIOR ART

A method of this type and a suitable IMS are known from International Patent Disclosure WO 97/38294 A1. With the known method, semivolatile substance traces are essentially collected by wiping off and concentrating onto a substrate made of inert carrier material. Then this substrate is quickly heated to vaporize the substance traces. The vapor is subsequently analyzed using conventional chemical analysis methods, particularly using an IMS.

IMS usually consist of a radioactivity ion source, which ionizes molecules of a sample gas within an ionization compartment of the IMS. Via a switchable grid, opened for brief periods of time, ion packages move into a drift compartment of the IMS where they are drawn via ring electrodes, arranged along a tube-shaped drift compartment, through an axial electric field.

Finally they encounter a collecting electrode at the opposite end of the drift compartment, where they generate a current that is amplified and measured. Since heavier ions are less mobile than light ions, they require a longer drift time. This means that the lighter ions from the original ion package arrive first and the heaviest last. After the pulsed opening of the switchable grid, the current is measured at the collecting electrode as a function of time. The intensity of the current at a prescribed point in time is thereby a measure for the concentration of ions of a specific mobility. The drift time and the mobility associated with it is then a measure for the respective mass of the ions.

The basic design of the IMS and its operation are known to the specialist. They are depicted in an overview, for example, in the textbooks "Ion Mobility Spectrometry" by G. A. Eiceman and Z. Karpas (CRC Press, 1994) and "Plasma Chromatography" ed. T. W. Carr (Plenum Press, 1984). Details will not be repeated here. However, it is understood that the invention depicted below can be used in combination with the known, prior art models of IMS.

Methods and equipment for the analysis of nonvolatile samples are known from U.S. Pat. Nos. 3,970,428; 4,220,414; 4,192,176; 5,405,781; 5,552,600 and 5,425,263. In U.S. Pat. No. 5,476,794, the suggestion is made to wipe off solid particles with a glove and then suction off the glove using a vacuum system.

In WO 93/06476 A1 and WO 96/37773 A1, IMS are described in which the sample gas is transported using a suction pulse.

Drug or explosive traces, in the form of grains with an average diameter between 1 and 10 micrometers, usually adhere to surfaces from which they can be wiped or suctioned off. For ionization, for example by proton transfer, these grains must first be broken down into molecules. The grains could attach ionized air molecules to their surface and receive a charge in this way. However, they then have too much mass overall to be transported within the IMS field.

For this reason, the substance traces must be heated to a high temperature so that they vaporize as completely as possible. Standard temperatures for heating the substrate range between 220 and 300° C. for the detection of explosives and drugs.

Due to the finite detection limit and the time response of the IMS detector, heating should take place as quickly as possible. Unfortunately, the molecules of interest, e.g. drugs or explosives, are not thermally resistant to any extent, they usually begin to decompose above about 150° C. This danger also exists for the substrate. However, if substance identification is based on fragments, the accuracy of identification drops. Hot metal surfaces promote the fragmentation process, and the molecule ions can penetrate into hot plastic surfaces which leads to losses in substance and a higher detection limit. In addition, so-called memory effects can lead to false alarms.

OBJECTIVE OF THE INVENTION

Therefore, a need exists for a detection method and an IMS in which the temperature increase for the vaporization of substance molecules is reduced. It is the objective of this invention to find such a method.

BRIEF DESCRIPTION OF THE INVENTION

The problem is solved in this invention by wetting the carrier material with a solvent, whereby molecules from the constituents are collected by the solvent and are vaporized together with the solvent. The constituent grains of the substance traces dissolve at least partially in the solvent and are then finely distributed. The molecules are isolated by dissolving in solvent and not by thermal breakdown of the grains. The vaporization process is therefore much gentler on the molecules. The relevant vaporization temperature depends on the solvent and thus is considerably lower than the vaporization temperature of the grains in the nonvolatile substances to be detected.

The lower vaporization temperature also reduces the energy consumption of the IMS, which is particularly important for handheld equipment.

As the solvent vaporizes, overpressure is created in the sample dispenser compartment. A drop of solvent corresponds to approx. 30 microliters of liquid and thus about 10 milliliters of vapor, which can lead to overpressure in the sample dispenser compartment of up to 10 bar. At a gas velocity through the sample dispenser of approx. 1 l/h, the overpressure is reduced in about 3 seconds. The overpressure is relieved, for example, by a narrow capillary toward the ion source of the IMS.

The solvent ions can, in a double function, also operate as a reagent gas and suppress interference gas signals if their proton affinity is between that of the interference gases and that of the substance molecules.

Particularly for drugs such as cocaine, heroin, cannabis and amphetarnines, the constituents are extremely proton-affine and the IMS operates at a positive polarity.

For explosives with nitro groups or wood preservatives with halogens, the constituents are electronegative and the IMS is operated at negative polarity.

The solvent is preferably an alcohol particularly ethanol. The solubility is quite good for most substances of interest. Alcohols are relatively nontoxic and easily available. Their vaporization temperature is low and their presence does not disturb the IMS measurement. When detecting drugs, their proton affinity can be exploited to suppress interference substance signals.

As an alternative, acetone can be used instead of an alcohol particularly for drug detection. Due to its even higher proton affinity, it is even better suited to elimite interference signals.

Particularly for the detection of explosives, carbon tetrachloride and methylene chloride are proven solvents.

Preferably, the carrier material is porous. In this way, grains of the substance to be detected can be captured on the one hand, and on the other hand, the surface is large enough to allow penetration of sufficient solvent.

The carrier material is preferably inert. This has the advantage that no interference signals are produced and no chemical changes appear in the substance that is to be detected.

In selecting a carrier material attention should be paid that it does not produce decomposition products when heating to the vaporization temperature, though reduced in comparison to the prior art, which impair the IMS measurement.

In one embodiment of the method, a contaminated surface, for example, is wiped off with the carrier material and the carrier material is then soaked with the solvent. As an alternative, the carrier material can also be soaked with the solvent and a surface is wiped off with the moist carrier material. A cloth soaked in solvent can be used as a carrier material particularly a commercially available moist cloth, with which a surface can be wiped off. On the other hand, the carrier material can also already contain the solvent in closed micropores, which can be opened before the IMS measurement, for example by squeezing or folding, so that the solvent escapes.

The substance traces can also be transferred to the carrier material by installing the carrier material in a dust-collecting device such as a filter. This is already known from the series of articles quoted at the outset. It is unnecessary to examine these more closely here.

With the method according to this invention, it is possible to keep the evaporation temperature considerably lower than the decomposition temperature of the constituents. Preferably, the temperature is less than 200° C., especially 150° C. The advantage of this is that the substances to be detected need not be recognized by their fragments, which increases detection accuracy.

A sample injector, particularly in the form of a narrow capillary, is preferably arranged between the sample dispenser and the ion source of the IMS. The injector extends only into the vicinity of the ion source. Transport of the molecules to be detected in the ion source, ie. the ionization compartment, occurs due to the release of overpressure resulting from the vaporizing solvent. In this way, the molecules fly from the end of the injector into the center of the reaction compartment. Preferably, the sample injector is a capillary of inert material particularly glass or quartz, which minimizes interference signals and memory effects.

The IMS includes heating devices for the sample dispenser, ion source and drift chamber, which are designed in such a way that they keep the sample dispenser at a temperature between 70° C. and 200° C., preferably between 90° C. and 160° C., and the ion source and the drift chamber of the IMS at temperatures between 50° C. and 150° C., preferably about 100° C. These are far lower temperatures than previously used in the prior art, which leads to the advantages mentioned in connection with the method according to the invention.

It is apparent that the features described above and continuing below need not be applied only in the respectively named combination, but also in any other combination or alone, without leaving the scope of the invention.

BRIEF DESCRIPTION OF THE FIGURES

The invention is explained more closely by means of embodiments and the drawing. These show.

FAVORABLE EMBODIMENTS

Figure 1:
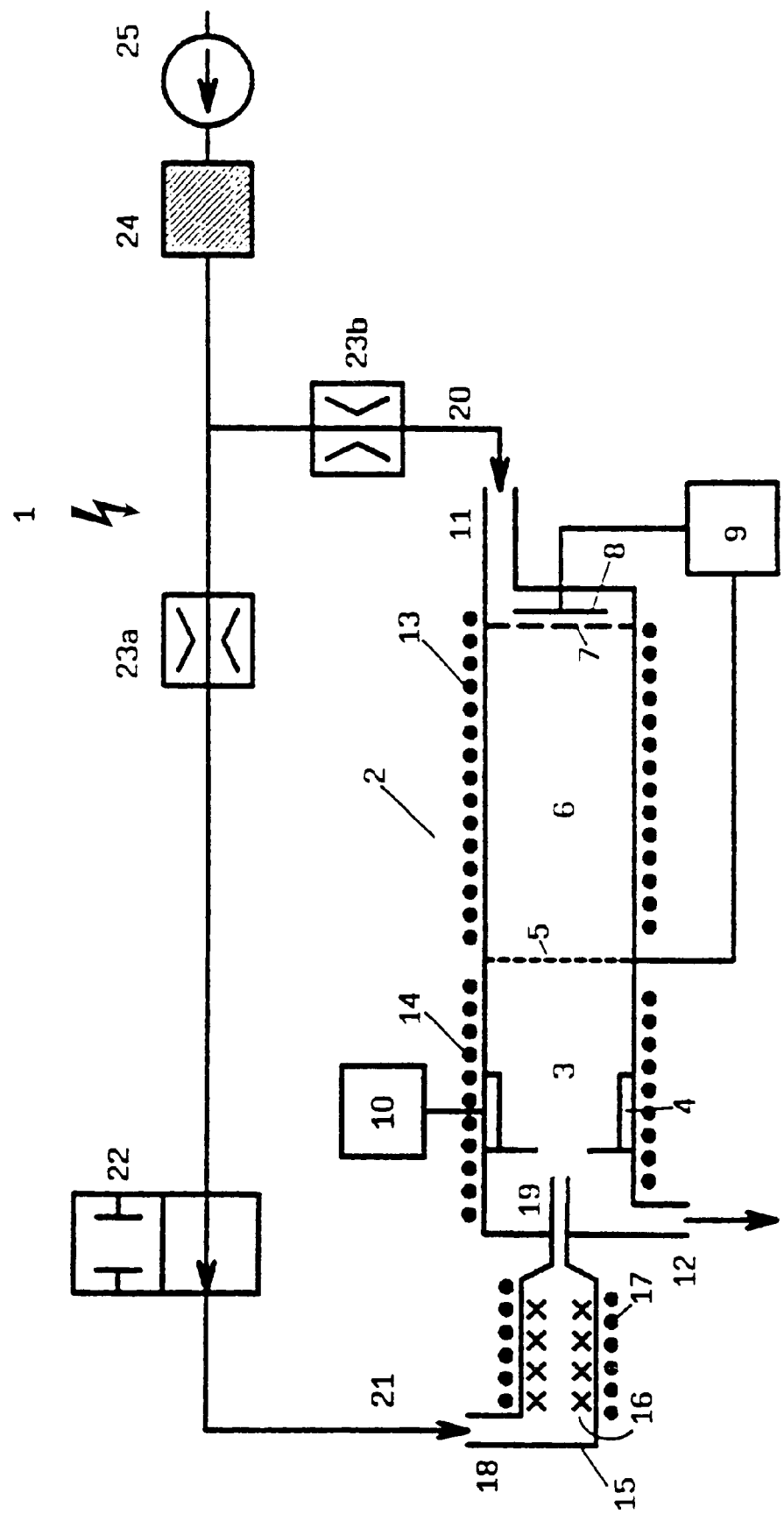
FIG. 1: Gas flow diagram for an embodiment of an ion mobility spectrometer according to the invention.

Specifically, FIG. 1 shows extremely schematically an IMS 1 with a measuring cell 2, a reaction compartment 3, which contains a radioactivity ion source 4, a switchable grid 5, a drift compartment 6, a screen grid 7 and an ion collector 8 as detector. The IMS 1, particularly the switchable grid 5 and the ion collector are controlled by a microcontroller 9. A high-voltage unit 10 supplies power to the IMS, particularly to the electrodes (not shown) of the drift chamber 6. Reaction compartment 3 and drift compartment 6 can be heated via separate heaters 13, 14.

Upstream from the actual IMS is a sample dispenser 15, in which a sample 16, generally in the form of solvent-soaked carrier material is introduced. The sample dispenser 15 can be heated via a heater 17. An injector 19 in the form of a capillary joins the sample dispenser 15 to the reaction compartment 3. The capillary 19 does not extend entirely into the area of the radiation source in the reaction compartment.

Through the pump 25, dry and clean compressed air is directed via filter 24 through the capillaries 23 a, b and pipelines 21 and 20 to the drift gas inlet 11 of the measuring cell 2, or to the carrier gas inlet 18 of the sample dispenser 15. This compressed air exits measuring cell 2 at gas outlet 12. In gas line 21, there is a solenoid 22.

In an initial operating mode, the solenoid 22 is closed at first. Once the heater 17 has been switched on, the vaporizing solvent generates a pressure surge which is released through the injector 19 into the reaction compartment 3. The sample molecules transported at the same time are then analyzed in the reaction compartment 3 by proton or charge transfer and detected in the usual manner by the IMS 1. To clear out the sample dispenser 15 after sample supply, the solenoid 22 is opened.

In a second operating mode, the solenoid 22 is also open during the sample supply. By selecting capillaries 23 a, b, a gas flow ratio of 10/1 is set between the lines 20 and 21.

The first operating mode is suitable for low concentrations, while the second produces less memory effects due to the continuing gas flow.

The temperature of the sample dispenser 15 is set at about 150° C. during operation, while the temperature in the reaction compartment 3 and the drift compartment 6 are usually about 100° C. After introducing the sample 16 into the sample dispenser 15, a measurement proceeds typically as a series of about 20 individual IMS measurements, which each consist of about 16 accumulated scans, which each lasts about 30 ms. The individual measurements follow one another at intervals of about 1 to 10 s. During the measurement, the solvent vaporizes completely and, at the same time, sweeps away any molecules of a contamination present with it. In the IMS spectrum, initially only an air ion peak is observed, then this disappears and is replaced by a strong peak from the solvent followed, in the case of contamination, by a weaker but clearly separate peak from the dissolved constituents, possibly accompanied by additional fragment peaks. Typically after about one minute, the contamination peak to be detected disappears again, and also the solvent peak somewhat later, while the air ion peak reappears.

Figure 2:
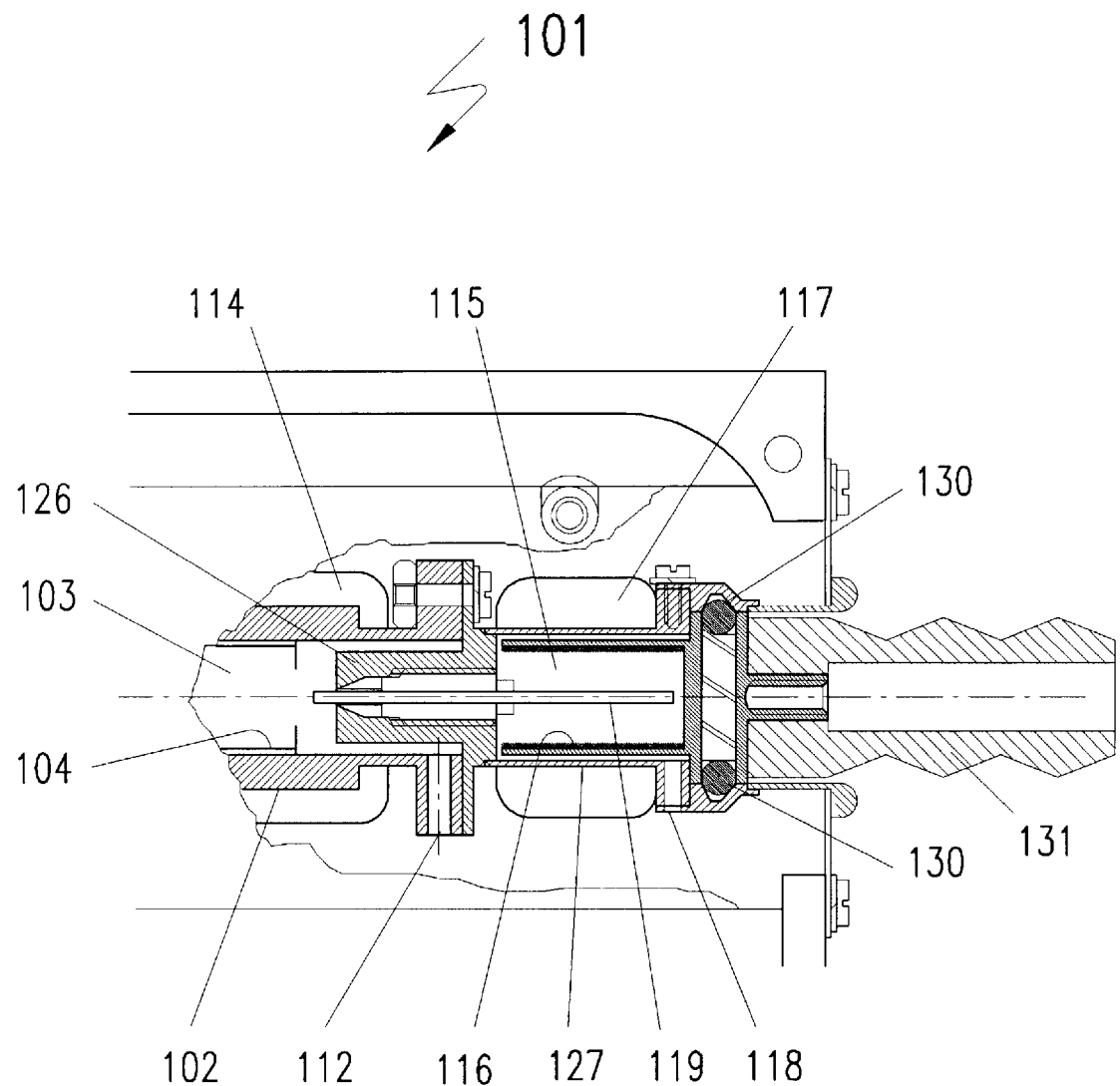
FIG. 2: Ion mobility spectrometer RAID 1 with sample dispenser according to the invention.

In FIG. 2, the sample dispenser range modified for performance of the method according to the invention is depicted from an embodiment of an IMS 101, which is distributed by the applicant under the label RAID 1. The reference numbers used are based on those in FIG. 1. Corresponding numbers, or those which designate the same or similar working parts, are raised by 100 from those in FIG. 1. At the left margin one can see part of the measuring cell 102 with the reaction compartment 103, in which there is a radiation source 104 in the form of a $^{63}$Ni hollow cylinder. The reaction compartment 103 is closed off on the right by a cover 126, in which a sample injector in the form of a quartz tube has been placed. The hollow cylindrical sample dispenser 115 is inserted into the sleeve 127 attached to the cover 126, and closed off gas-tight via a sealing ring 130 opposite the outer compartment. The sample dispenser 115 has a diameter of about 1 cm and, by means of a grip 131, can be inserted and locked or removed. The measuring air flows, on the one hand, along the measuring cell 102 to the gas outlet 112 of the reaction compartment 103 and, on the other hand, in the corresponding operating mode, through the carrier gas inlet 118 into the sample dispenser 115 and from there, together with the solvent vaporizing from the sample 116, through the quartz tube 119 into the reaction compartment. The sample dispenser 115 and also the sample 116 are heated during operation by the sample dispenser heater to 117 to 150° C. typically. In this way the solvent vaporizes from the sample 116 and takes any dissolved molecules from the contamination with it. Thus an overpressure results in the sample dispenser 115, which first collects and then is released through the quartz capillary 119 into the reaction compartment 103. Only a small part of the quartz tube 119 projects into the reaction compartment 103 and stops particularly in front of the hollow cylindrical radiation source 104. In this way, interfering field distortions are prevented in the reaction source area, which result as soon as an object is inserted into the radiation source 104, regardless of whether it is a metal or an insulator. Due to the overpressure, the solvent vapor with the dissolved molecules nevertheless reaches the inside of the radiation source 104, so that a charge transfer or proton transfer take place. While the solvent vaporizes, IMS spectra are recorded over a period of time of about one minute periodically through the RAID spectrometer 101 and are displayed. Here, the spectrometer operates in a conventional operating mode with negative polarity for electronegative substances and positive polarity for proton-affine substances. The temperature of the measuring tube 102 from reaction compartment 103 and drift compartment 106 is maintained here at about 100° C.

Figure 3:
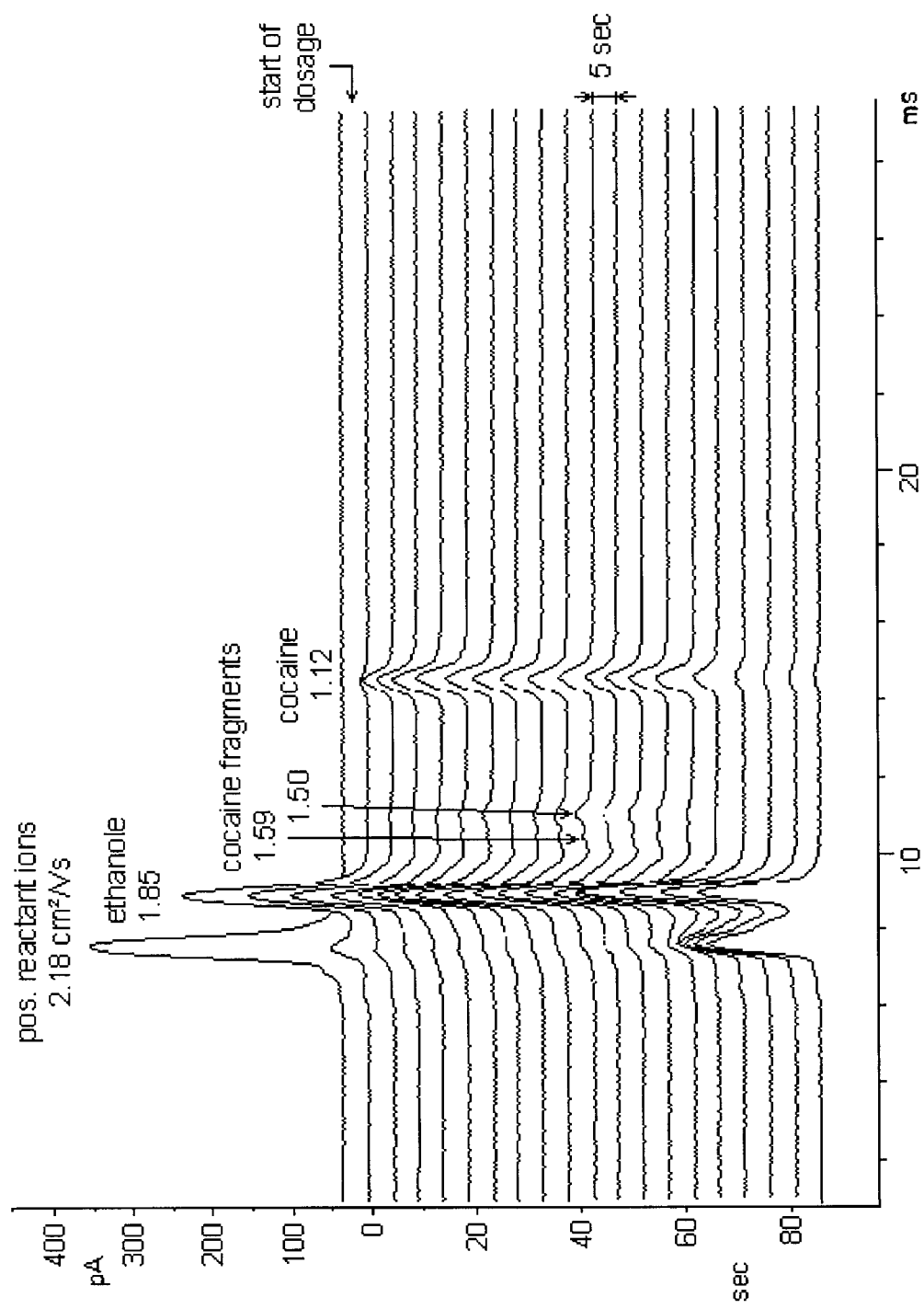
FIG. 3: IMS spectrum of an alcoholic cocaine solution on paper.

FIG. 3 shows a spectrum scanned in such a manner of an alcoholic (ethanol) solution of 0.1 ng cocaine per microliter solution applied to 1 $cm^2$ paper. The total amount was 30 microliters. The temperature of the sample dispenser was 150° C., that of the IMS tube 100° C. A drift gas current of air flowed through the tube at 10 l/h while the carrier gas stream through the sample dispenser was 1 l/h air.

After metering was started, spectra were produced in the positive operating mode of the RAID 1 spectrometer at intervals of 5 s. At the same time, 16 individual measurements of 30 ms duration each were accumulated per spectrum. The measurements depicted in FIG. 3 are staggered. Initially, only an air ion peak can be seen at $K_0=2.18$ $cm^2/Vs$, which already almost disappears within the first 5 s. At the same time, the peak characteristic for ethanol appears at $K_0=1.85$ $cm^2/Vs$. Already after 5 s, a small but clear peak can be seen at $K_0=1.12$ $cm^2/Vs$, which characterizes cocaine. This peak continues to grow within about one minute and then slowly disappears again. After one minute, the air ion peak also reappears and the solvent peak (ethanol) decreases. In addition to the purely cocaine peak at $K_0=1.12$ $cm^2/Vs$, two small peaks can also be seen very weakly at $K_0=1.59$ $cm^2/Vs$ and $K_0=1.50$ $cm^2/Vs$, which correspond to cocaine fragments.

The detection limit for cocaine is currently at about 0.1 ng.

Figure 4:
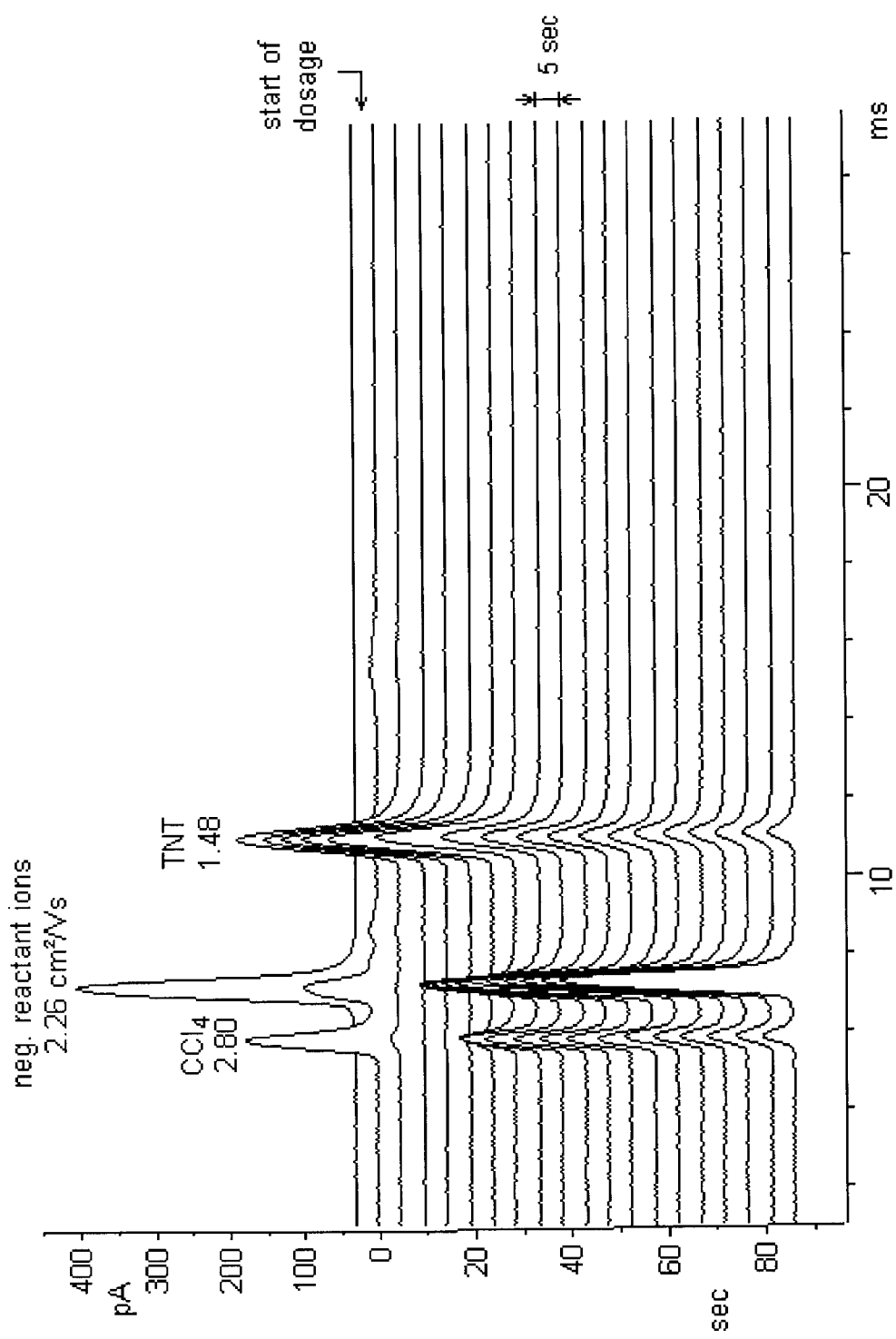
FIG. 4: IMS spectrum of a TNT solution in carbon tetrachloride.

FIG. 4 shows an example of the method according to the invention with negative polarity of the RAID 1 spectrometer for detection of the explosive TNT. FIG. 4 shows a spectrum, recorded in such a manner, of a solution of 17 ng TNT per microliter solution in carbon tetrachloride applied to 1 $cm^2$ paper. The total amount was 30 microliters. The temperature of the sample dispenser was 147° C., that of the IMS tube 100° C. A gas current flowed through the tube with 10.7 l/h air, while the carrier gas stream through the sample dispenser was 1.2 l/h air.

After sample supply was started, 20 individual spectra over 16 measurements each of 30 ms duration each were accumulated again. They were produced at intervals of 5.05 s in the negative operating mode of the RAID 1 spectrometer. The measurements depicted in FIG. 4 are staggered. The total measuring time was 1.68 min. Initially only a negative air ion peak can be seen at $k_0=2.26$ $cm^2/Vs$, which almost disappears again already within the first 5 s. At the same time, the peak characteristic for $CCl_4$ appears at $k_0=2.80$ $cm^2/Vs$. Already after 5 s, a very intensive, clear peak can also already be seen at $k_0=1.48$ $cm^2/Vs$, slowly decreases. In the initial phase, even the solvent peak is completely suppressed. After about a half a minute, the air ion peak and the solvent peak appear again, while the TNT peak decreases.

What is claimed is:

1. Method for detection of traces of semivolatile dangerous compounds with an ion mobility spectrometer (IMS), comprising the following steps:
   a) applying the compound traces on a dry or wet carrier material,
   b) wetting the compound traces on the carrier material by a solvent, thereby solving some molecules of the traces,
   c) introducing the wet carrier material into a sample dispenser,
   d) heating the carrier material inside the sample dispenser to a vaporization temperature, whereby solvent and compounds are released as vapors from the carrier material,
   e) transporting the vapors into an ion source of the IMS, f) ionizing molecules of the compounds by proton or charge transfer, passing the ions through an IMS drift chamber, detecting ion current as a function of time, and identifying the ions by their mobility.

2. Method as in claim 1, wherein the compounds are proton-affine, and the IMS is operated at positive polarity.

3. Method as in claim 1, wherein the compounds are electronegative, and the IMS is operated at negative polarity.

4. Method as in claim 1, wherein the solvent is an alcohol.

5. Method as in claim 1, wherein the solvent is comprised of one or more of acetone, carbon tetrachloride, and methylene chloride.

6. Method as in claim 1, wherein the carrier material is porous.

7. Method as in claim 1, wherein the carrier material is inert.

8. Method as in claim 1, wherein the carrier material produces no decomposition products impairing the IMS measurement when heated.

9. Method as in claim 1, wherein a surface is wiped off with the carrier material and the carrier material is then soaked with the solvent.

10. Method as in claim 1, wherein the carrier material is soaked with the solvent and a surface is wiped off with the moist carrier material.

11. Method as in claim 10, wherein a cloth soaked with the solvent is used as a carrier material with which a surface is wiped off.

12. Method as in claim 1, wherein the carrier material contains the solvent in closed micropores, which are opened before the IMS measurement so that the solvent escapes.

13. Method as in claim 1, wherein the compound traces reach the carrier material by the fact that the carrier material is installed in a dust-collecting device as a filter.

14. Method as in claim 1, wherein the vaporization temperature is lower than a decomposition temperature of the compound traces.

15. Method as in claim 1, wherein the vaporization temperature is lower than 200° C.

16. Method as in claim 1, wherein a sample injector is arranged between the sample dispenser and the ion source of the IMS.

17. Method as in claim 16, wherein the sample injector is comprised of a capillary of inert material.

18. IMS to perform a method according to claim 1, wherein heating devices are provided which keep a sample dispenser at a temperature between 70° C. and 200° C. and keep the ion source and drift chamber at temperatures between 50° C. and 150° C.

19. IMS according to claim 18, wherein a sample injector is provided between the sample dispenser and the ion source.

20. IMS according to claim 19, wherein the sample injector is a capillary.

21. IMS according to claim 20, wherein the capillary does not project into the ion source.

* * * * *

UNITED STATES PATENT AND TRADEMARK OFFICE
CERTIFICATE OF CORRECTION

PATENT NO. : 6,144,029
DATED : November 7, 2000
INVENTOR(S) : Joachim Adler, Frank Laukien It is certified that error appears in the above-identified patent and that said Letters Patent is hereby corrected as shown below:

<u>Title page,</u>
Item [75] INVENTOR, after "Joachim Adler, Badrina, Germany", please insert -- Frank Laukien, Lincoln, Massachusetts --.

Signed and Sealed this

Second Day of October, 2001

Attest:

NICHOLAS P. GODICI
Attesting Officer    Acting Director of the United States Patent and Trademark Office